(12) United States Patent
Bialik (10) Patent No.: US 12,064,274 B2
(45) Date of Patent: Aug. 20, 2024

(54) RADIOLUCENT MAT AND IMAGE RECEPTOR ASSEMBLY INCLUDING SAME

(71) Applicant: Ariel Eli Bialik, Fargo, ND (US)

(72) Inventor: Ariel Eli Bialik, Fargo, ND (US)

(73) Assignee: Ariel Eli Bialik, Fargo, ND (US)

(*) Notice: Subject to any disclaimer, the term of this patent is extended or adjusted under 35 U.S.C. 154(b) by 284 days.

(21) Appl. No.: 17/446,357

(22) Filed: Aug. 30, 2021

(65) Prior Publication Data

US 2022/0233155 A1    Jul. 28, 2022

Related U.S. Application Data

(60) Provisional application No. 63/141,469, filed on Jan. 25, 2021.

(51) Int. Cl.
*A61B 6/04* (2006.01)
*A61B 6/42* (2024.01)

(52) U.S. Cl.
CPC .......... *A61B 6/0407* (2013.01); *A61B 6/4216* (2013.01)

(58) Field of Classification Search
CPC ....... A61B 6/0407; A61B 6/0492; A61B 6/42; A61B 6/12; A61B 6/4283; A61B 6/4208; A61B 6/4216; A61B 6/4233
See application file for complete search history.

(56) References Cited

U.S. PATENT DOCUMENTS

| | | | | |
|---|---|---|---|---|
| 3,191,032 A | * | 6/1965 | Buck | G03B 42/04 378/188 |
| 4,045,678 A | * | 8/1977 | Rickard | A61B 6/501 5/601 |
| 4,156,145 A | * | 5/1979 | Weatherholt | A61B 6/0442 378/177 |
| 4,166,958 A | * | 9/1979 | Haselbarth | G03B 42/04 378/188 |
| 4,895,173 A | | 1/1990 | Brault et al. | |
| 5,166,968 A | * | 11/1992 | Morse | A61B 6/04 5/601 |

(Continued)

FOREIGN PATENT DOCUMENTS

WO    2009/008325 A1    1/2019

OTHER PUBLICATIONS

International Search Report issued in PCT/US2022/040319, mailed Nov. 2, 2022, 2 pages.

(Continued)

*Primary Examiner* — Dani Fox
*Assistant Examiner* — Soorena Kefayati
(74) *Attorney, Agent, or Firm* — Faegre Drinker Biddle & Reath LLP (57) ABSTRACT

A radiolucent mat includes a strap system configured to secure the radiolucent mat to an image receptor, and a body portion extending along orthogonal length and width directions of the body portion and including a top major surface configured to face away from the image receptor. The top major surface includes one or more first visual indicia delineating a region of the top major surface corresponding to an active region of the image receptor. An image receptor assembly includes the radiolucent mat and a radiography image receptor having an active region. The body portion is disposed on the image receptor such that the body portion and the image receptor are substantially coextensive with one another along the length and width directions.

19 Claims, 8 Drawing Sheets

(56) References Cited

U.S. PATENT DOCUMENTS

| | | | | |
|---|---|---|---|---|
| 6,893,156 | B2* | 5/2005 | Sharpensteen | G03B 42/025 5/601 |
| 7,431,498 | B2* | 10/2008 | Youngblood-Johnson | G03B 42/02 378/177 |
| 7,632,013 | B1* | 12/2009 | Bueltmann | G03B 42/04 378/204 |
| 2002/0181658 | A1* | 12/2002 | Garcia | A61B 6/51 378/168 |
| 2003/0099325 | A1* | 5/2003 | Galkin | A61B 6/0414 378/37 |
| 2004/0156472 | A1* | 8/2004 | Galkin | A61B 6/4283 378/37 |
| 2005/0198736 | A1* | 9/2005 | Jahrling | A61B 6/4423 5/601 |
| 2007/0019785 | A1* | 1/2007 | Galkin | A61B 6/0414 378/37 |
| 2008/0240357 | A1* | 10/2008 | Jabri | A61B 6/5252 378/154 |
| 2009/0213997 | A1* | 8/2009 | Maschke | A61B 6/04 378/208 |
| 2009/0316861 | A1* | 12/2009 | Behle | G03B 42/04 378/182 |
| 2021/0228311 | A1* | 7/2021 | Galili | A61B 50/20 |

OTHER PUBLICATIONS

"Diagnostic Imaging Foam Table Pads Imaging Table Foam Pads." Universal Medical, www.universalmedicalinc.com/all-products/diagnostic-imaging/foam-imaging-table-pads.html. Accessed Oct. 10, 2023.

* cited by examiner

RADIOLUCENT MAT AND IMAGE RECEPTOR ASSEMBLY INCLUDING SAME

BACKGROUND

Bone surveys of infants and other infant imaging procedures can be carried out by placing the infant directly on an image receptor.

SUMMARY

In some aspects of the present description, a radiolucent mat is provided. The radiolucent mat includes a strap system configured to secure the radiolucent mat to an image receptor, and a body portion extending along orthogonal length and width directions of the body portion and including a top major surface configured to face away from the image receptor. The top major surface can include one or more first visual indicia delineating a region of the top major surface corresponding to an active region of the image receptor. The strap system includes a first strap extending from a first side of the body portion; a first connector for receiving the first strap disposed adjacent a second side of the body portion opposite the first side, where the first and second sides extend along the length direction and are spaced apart along the width direction; a second strap extending from one of the first and second sides of the body portion; a second connector for receiving the second strap disposed adjacent the other of the first and second sides, where the first and second straps extend from respective first and second locations of the body portion spaced apart along the length direction by greater than 0.3 times a length of the body portion along the length direction; a third strap extending from a third side of the body portion; a third connector for receiving the third strap disposed adjacent a fourth side of the body portion opposite the third side, where the third and fourth sides extend along the width direction and are spaced apart along the length direction; and a fourth strap extending from one of the third and fourth sides of the body portion; and a fourth connector for receiving the fourth strap disposed adjacent the other of the third and fourth sides, where the third and fourth straps extend from respective third and fourth locations of the body portion spaced apart along the width direction by greater than 0.3 times a width of the body portion along the width direction.

In some aspects of the present description, a radiolucent mat is provided. The radiolucent mat includes a strap system configured to secure the radiolucent mat to an image receptor and a body portion extending along orthogonal length and width directions of the body portion and including a top major surface configured to face away from the image receptor. The top major surface includes one or more first visual indicia delineating a region of the top major surface corresponding to an active region of the image receptor. The strap system includes a first strap extending from a first location of a first side of the body portion, where the first location is substantially centered on the first side along the length direction; a first connector for receiving the first strap disposed adjacent a second side of the body portion opposite the first side, where the first and second sides extend along the length direction and are spaced apart along the width direction; a second strap extending from a third side of the body portion; a second connector for receiving the second strap disposed adjacent a fourth side of the body portion opposite the third side, where the third and fourth sides extend along the width direction and are spaced apart along the length direction; a third strap extending from one of the third and fourth sides of the body portion; and a third connector for receiving the third strap disposed adjacent the other of the third and fourth sides, where the second and third straps extending from respective second and third locations of the body portion spaced apart along the width direction by greater than 0.3 times a width of the body portion along the width direction.

In some aspects of the present description, an image receptor assembly is provided. The image receptor assembly includes a radiolucent mat comprising a body portion extending along orthogonal length and width directions of the body portion, and a radiography image receptor having an active region. The body portion is disposed on the image receptor such that the body portion and the image receptor are substantially coextensive with one another along the length and width directions. The radiolucent mat includes a strap system securing the radiolucent mat to the image receptor and preventing the radiolucent mat from moving relative to the image receptor along each of the length and width directions. The body portion includes a top major surface facing away from the image receptor. The top major surface can include one or more visual indicia delineating a region of the top major surface corresponding to the active region of the image receptor. The region of the top major surface may be smaller than the active region of the image receptor.

These and other aspects will be apparent from the following detailed description. In no event, however, should this brief summary be construed to limit the claimable subject matter.

DETAILED DESCRIPTION

In the following description, reference is made to the accompanying drawings that form a part hereof and in which various embodiments are shown by way of illustration. The drawings are not necessarily to scale. It is to be understood that other embodiments are contemplated and may be made without departing from the scope or spirit of the present description. The following detailed description, therefore, is not to be taken in a limiting sense.

Bone surveys of infants, and other infant imaging procedures on a tabletop (e.g., placing the infant directly on a radiography image receptor disposed on a tabletop), to perform and capture radiographs (x-ray images) are a common occurrence in many radiography settings. However, the image receptor (e.g., a digital radiography digital image receptor, or a computed radiography photostimulable phosphor plate, or a film radiography image receptor) typically has a firm, hard surface. When an infant is placed on top of a firm, hard surface such as a that of an image receptor, the infant will often begin to cry, scream, and struggle during the imaging process. The discomfort and lack of cooperation from the infant laying on this hard surface will typically increase as the imaging process on the hard surface progresses. Bone surveys on infants often are a lengthy process that can involve a couple dozen or more imaging positions and consequent radiographs. Unanticipated movement by the baby during the imaging procedures, as well as a lack of cooperation from the infant, can result in many unnecessary repeats that could otherwise have been prevented had the infant been laying on a (e.g., slightly) cushioned surface. Thus, bone surveys and other infant imaging procedures often take longer to complete when the infant is uncomfortable due to laying on a hard image receptor surface. Furthermore, when infants are laying on a hard imaging receptor the process of restraining and restricting the movements of the uncooperative infant can result in the baby injuring itself while struggling against the radiographer. However, placing a conventional table pad (e.g., commercially available table pads commonly used for adults) on the image receptor typically results in other problems. For example, it can be difficult to determine where the infant should be placed on the pad relative to an active region of the image receptor. This problem can be exasperated by movement of the pad relative to the image receptor during the imaging process. As another example, a conventional table pad can result in reduced spatial resolution of the resulting image due to the magnification arising from the increase in object to image distance (OID) resulting from the thickness of the table pad.

According to some embodiments of the present description, a radiolucent mat is provided that is suitable for infant imaging procedures without many of the problems associated with placing the infant on a hard surface of an image receptor or on a conventional table mat disposed on an image receptor. In some embodiments, the radiolucent mat includes a strap system for secure the radiolucent mat to an image receptor and may also include one or more indica delineating a region of a top major surface of a body portion of the radiolucent mat that corresponds to an active region of the image receptor. The body portion can be aligned with the image receptor. For example, the body portion and the image receptor can be substantially coextensive (e.g., at least 80 or 90 percent by area of the body portion can be coextensive with at least 80 or 90 percent by area of the image receptor, or the body portion can be coextensive with the image receptor except that the image receptor may include optional handle(s) not covered by the body portion) with one another such that (e.g., at least 3 or all 4 of the) edges of the mat are aligned with corresponding edges of the image receptor along the length and width directions of the body portion. The strap system can secure the mat to the image receptor to prevent the mat from moving relative to the image receptor along each of length and width directions of the body portion. The strap system may include at least three straps arranged (e.g., suitably spaced apart) to stably secure the mat to the image receptor. The radiographer performing x-rays on the patient will then know that the image receptor is directly underneath the mat and that the edges of the mat correspond to the edges of the image receptor. The one or more indica can reliably indicate the region of the mat corresponding to the active region of the image receptor. Furthermore, according to some embodiments, the thickness of the body portion of the mat can be thinner than that of conventional table pads used in imaging in order to reduce the increase in OID resulting from the thickness. The region of the mat delineated by the one or more indicia can be smaller than the corresponding active region of the image receptor to account for typical divergence of radiation from a radiation source (e.g., x-ray tube) through the thickness of the body portion.

Figure 1:
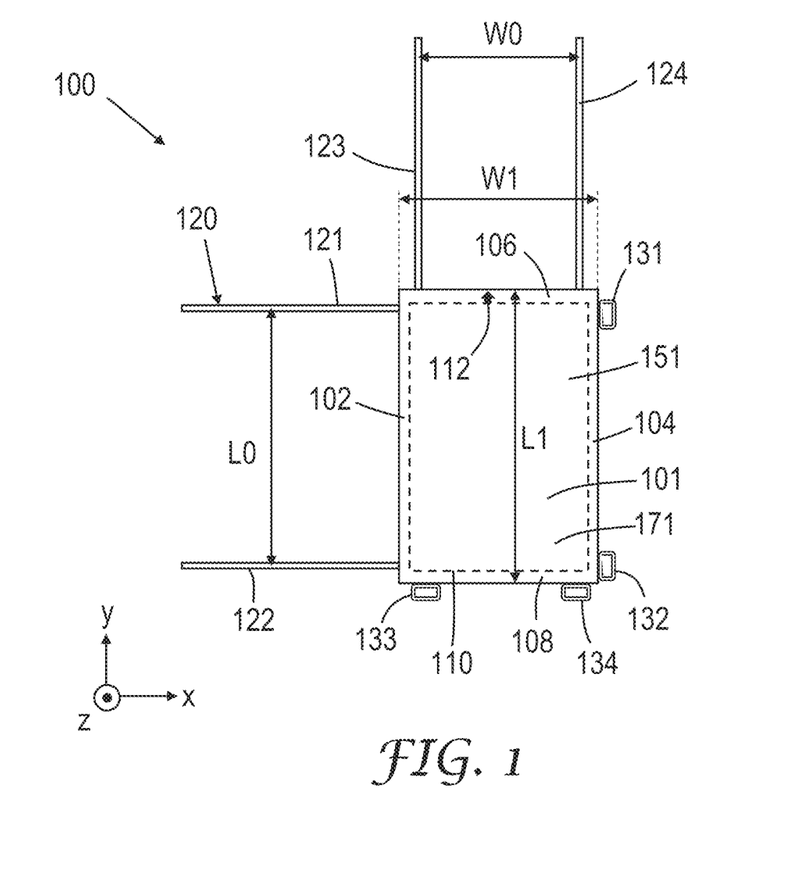
FIGS. 1-2 are schematic top views of radiolucent mats, according to some embodiments.
Figure 2:
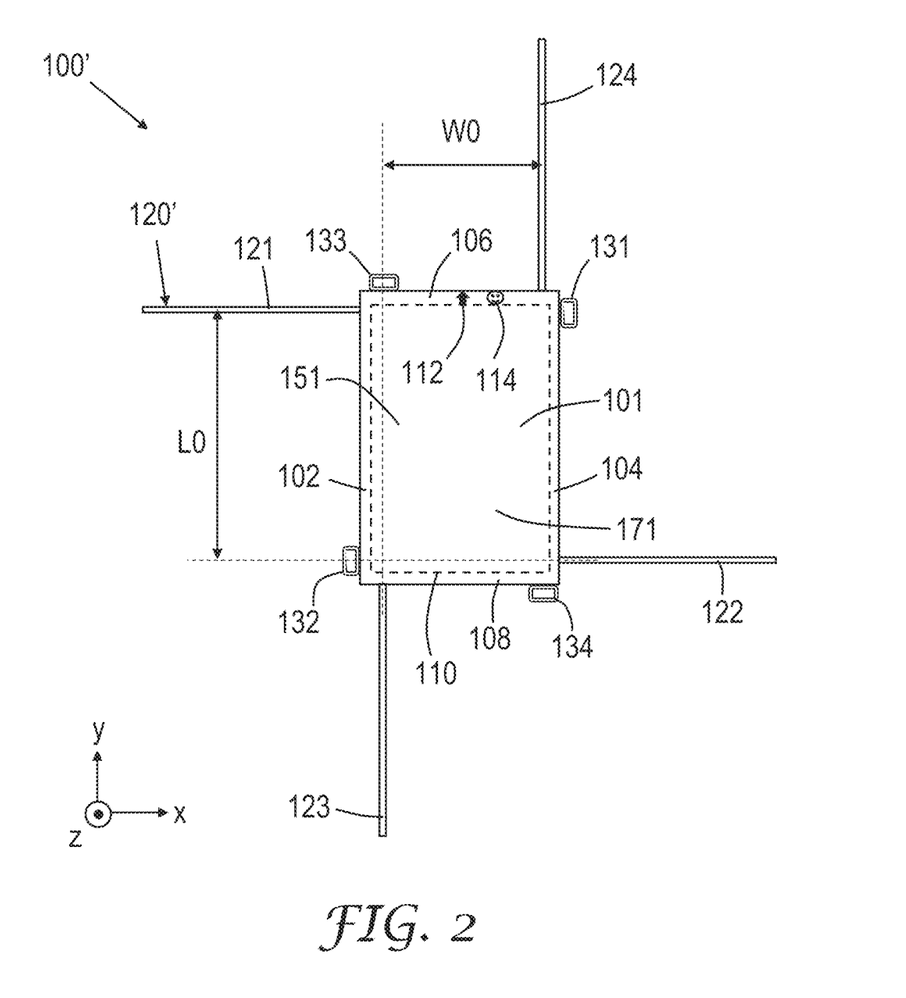
Figure 3:
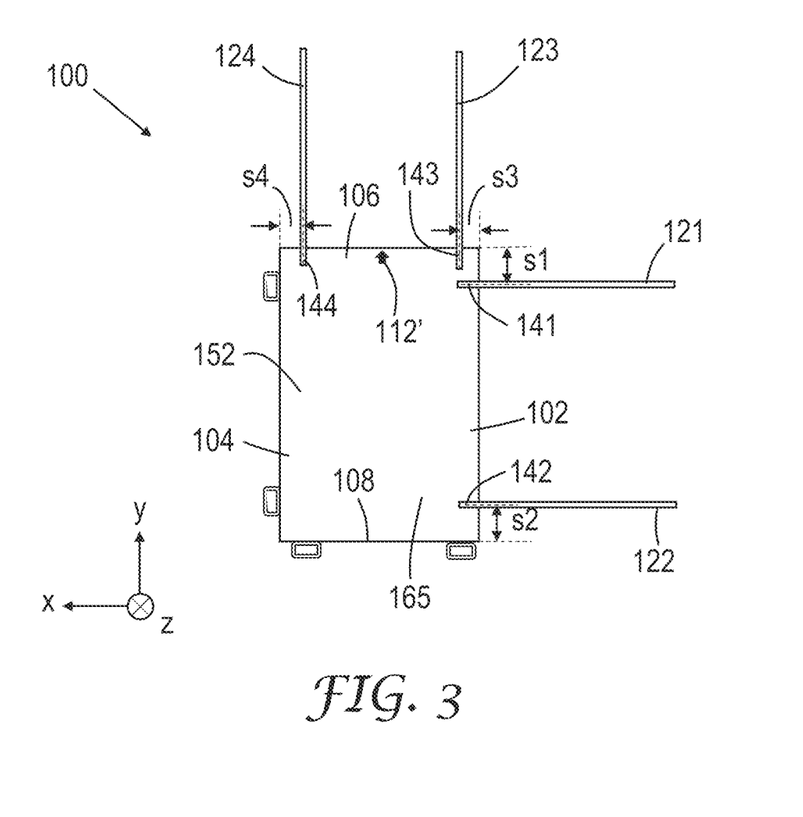
FIGS. 3-5 are schematic bottom views of radiolucent mats, according to some embodiments.
Figure 4:
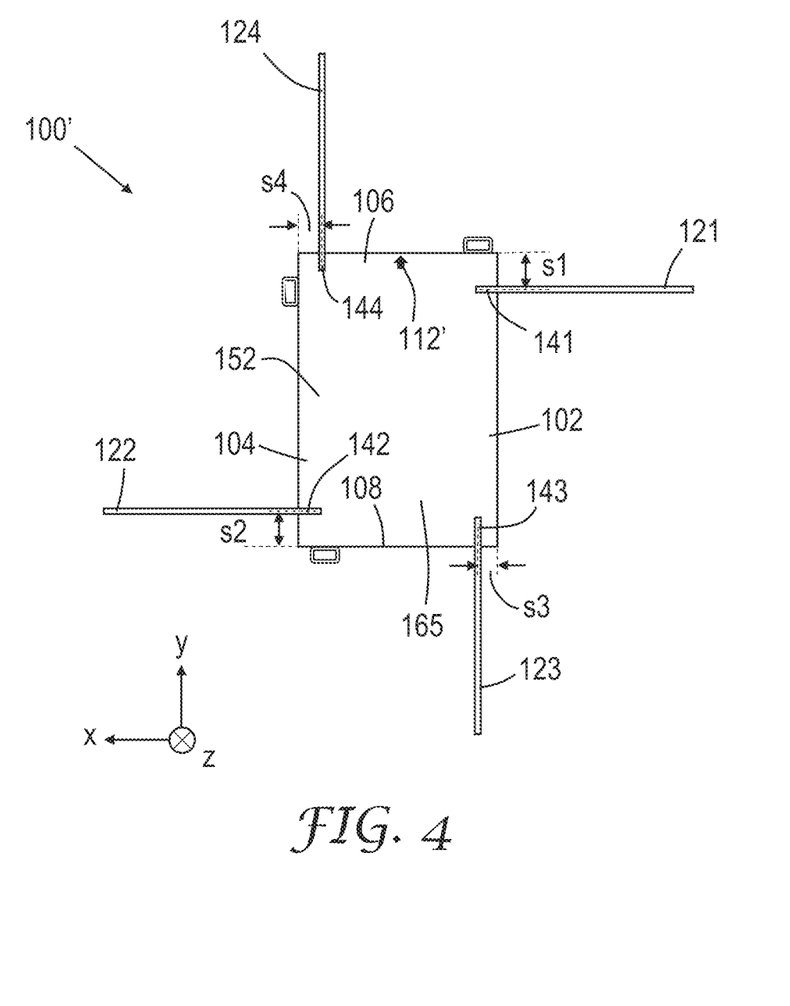
Figure 5:
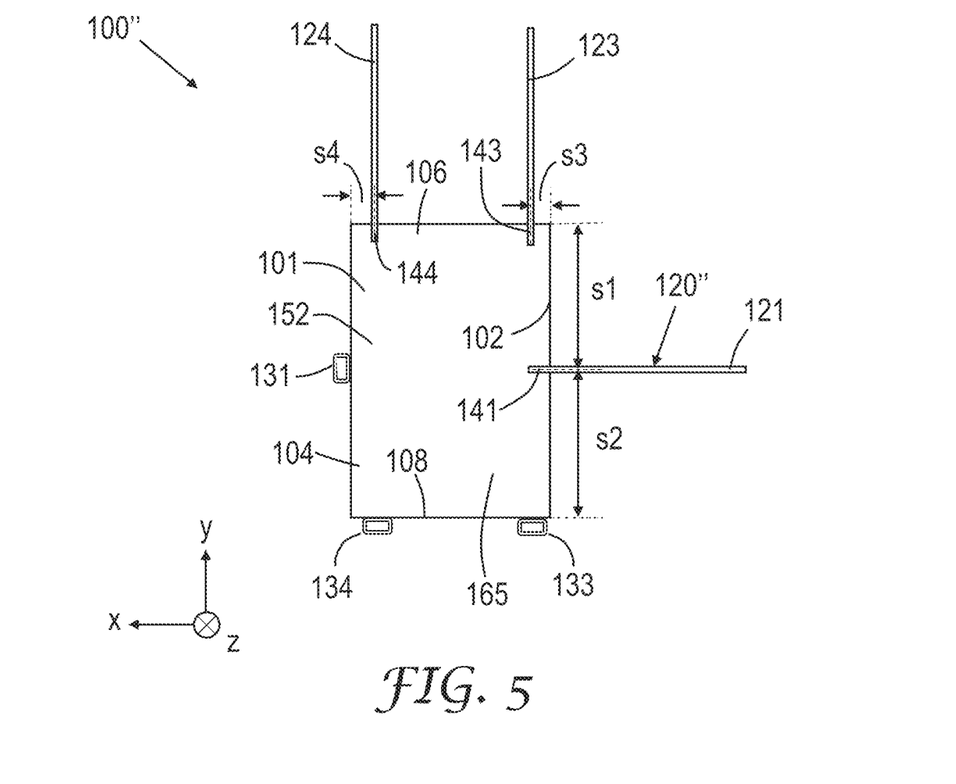

FIGS. 1-2 are schematic top views of radiolucent mats 100 and 100', according to some embodiments. FIGS. 3-4 are schematic bottom views of the respective radiolucent mats 100 and 100', according to some embodiments. FIG. 5 is a schematic bottom view of a radiolucent mat 100", according to some embodiments. The radiolucent mat 100, 100', 100" includes a body portion 101 and a strap system 120, 120', 120" configured to secure the radiolucent mat to an image receptor (see, e.g., image receptor 250 schematically illustrated in FIG. 8). The radiolucent mat 100, 100', 100" includes a body portion having dimensions of W1 by L1 which can correspond to the width and length of a conventional image receptor. For example, W1 can be about 13 to 19 inches and L1 can be about 17 to 20 inches (e.g., for a conventional full-sized image receptor). As another example, W1 can be about 9 to 13 inches or about 10 to 12 inches, and L1 can be about 10 to 17 inches or about 12 to 14 inches (e.g., for a portable image receptor that can be used for mobile imaging of infants and/or can fit into a crib). In some embodiments, the radiolucent mat has a body portion dimensioned to be substantially coextensive with an image receptor having an active area of about 14 to 17 inches by about 17 inches or having an active area of about 9 to 11 inches by about 12 to 14 inches.

In some embodiments, a radiolucent mat 100, 100', 100" includes a strap system 120, 120', 120" configured to secure the radiolucent mat to an image receptor, and a body portion 101 extending along orthogonal length (y-direction) and width (x-direction) directions of the body portion 101. The body portion 101 includes a top major surface 151 configured to face away from the image receptor and an opposite bottom major surface 152.

In some embodiments, the strap system 120, 120' includes a first strap 121 extending from a first side 102 of the body portion 101; a first connector 131 for receiving the first strap disposed adjacent a second side 104 of the body portion 101 opposite the first side 102, where the first and second sides 102 and 104 extend along the length direction and are spaced apart along the width direction; a second strap 122 extending from one of the first and second sides of the body portion 101 (for strap system 120, second strap 122 extends from the first side 102; and for strap system 120', second strap 122 extends from the second side 104); a second connector 132 for receiving the second strap disposed adjacent the other of the first and second sides; a third strap 123 extending from a third side 106 of the body portion; a third connector 133 for receiving the third strap disposed adjacent a fourth side 108 of the body portion opposite the third side 106, where the third and fourth sides 106 and 108 extend along the width direction and are spaced apart along the length direction; a fourth strap 124 extending from one of the third and fourth sides of the body portion 101 (for strap system 120, fourth strap 124 extends from the third side 106; and for strap system 120', fourth strap 124 extends from the fourth side 108); and a fourth connector 134 for receiving the fourth strap disposed adjacent the other of the third and fourth sides.

In some embodiments, the strap system 120, 120' includes only 4 straps as schematically illustrated in FIGS. 1-4. In other embodiments, a different number of straps (e.g., 3 as illustrated in FIG. 5 or more than 4) may be used. The strap system generally includes at least one strap along the length direction (e.g., one strap substantially centered along the length direction or two or more straps spaced apart along the length direction) and at least one strap along the width direction (e.g., one strap substantially centered along the width direction or two or more straps spaced apart along the width direction). For example, the strap system may include a set of three or more straps arranged along the length direction, and a set of two or more straps arranged along the width direction. A total of at least three straps is generally preferred to prevent the mat from moving relative to the image receptor along each of length and width directions of the body portion. Including at least two straps along each of the length and width directions may be preferred in some embodiments to allow the mat to be more firmly and stably fixed to the image receptor than, for example, using a single strap along each of the length and width directions, while in other embodiments, a fewer number of straps may be preferred due to, for example, the geometry of the image receptor (see, e.g., FIG. 12).

In some embodiments, the strap system 120" includes only one strap 121 along the length direction as schematically illustrated in FIG. 5, for example. A single strap along the length direction may be desired for some image receptors where the image receptor includes a handle that might otherwise interfere with the placement of more than one strap along the length direction (see, e.g., FIG. 12). In some embodiments, the strap system 120" includes a first strap 121 extending from a first location 141 of a first side 102 of the body portion; a first connector 131 for receiving the first strap 121 disposed adjacent a second side 104 of the body portion 101 opposite the first side 102, where the first and second sides 102 and 104 extend along the length direction and are spaced apart along the width direction; a second strap 123 extending from a third side 106 of the body portion 101; a second connector 133 for receiving the second strap 123 disposed adjacent a fourth side 108 of the body portion 101 opposite the third side 106, where the third and fourth sides 106 and 108 extend along the width direction and are spaced apart along the length direction; a third strap 124 extending from one of the third and fourth sides of the body portion (e.g., from the third side 106 as schematically illustrated in FIG. 5 or from the fourth side 108 as schematically illustrated in FIG. 4); and a third connector 134 for receiving the third strap 124 disposed adjacent the other of the third and fourth sides, where the second and third straps extend from respective second and third locations 143 and 144 of the body portion spaced apart along the width direction by greater than 0.3 times a width of the body portion along the width direction. In some embodiments, the first location 141 is substantially centered on the first side 102 along the length direction (e.g., closer to a center of the first side 102 along the length direction than to either of the third and fourth sides 106 and 108). Similarly, in some embodiments, the first connector is substantially centered on the second side 104 along the length direction. In some embodiments, a largest separation s1 of the first location 141 from the third side 106 along the length direction is within 25%, or 20%, or 15%, or 10%, or 5% of a largest separation s2 of the first location 141 from the fourth side 108 along the length direction. The radiolucent mat 100" can optionally include straps 123 and 124 extending from opposite sides of the body portion 101 as schematically illustrated in FIGS. 2 and 4, for example. The radiolucent mat 100" can optionally include any of the indicia 112, 112', 114 schematically illustrated in FIGS. 1-4.

Any suitable strap and connector system known in the art may be used. For example, a strap and buckle system may be used. In some embodiments, the strap system is configured such that once the body portion is disposed on an image receptor and edges of the body portion are aligned with corresponding edges of the image receptor, the radiographer can pull the respective straps underneath the image receptor and attach the strap to the connector on the opposite side of the body portion (see, e.g., FIGS. 10-12). Typically, the radiographer can then tighten the strap so that the mat will not slide back and forth on top of the image receptor while also ensuring that edges of the mat align with corresponding edges of the image receptor.

In some embodiments, there is significant separation along the length direction between the first and second straps 121 and 122 and/or significant separation along the width direction between the third and fourth straps 123 and 124 (also referred to as second and third straps when strap 122 is omitted as schematically illustrated in FIG. 5). Such separation can allow the strap system to stably secure the mat to the image receptor and prevent the mat from moving relative to the image receptor along each of the length and width directions. In some embodiments, the first and second straps 121 and 122 extend from respective first and second locations (see, e.g., locations 141 and 142 schematically illustrated in FIGS. 3-4) of the body portion spaced apart (by distance L0) along the length direction by greater than 0.3, 0.4, 0.5, 0.6, 0.65, 0.7, or 0.75 times a length L1 of the body portion along the length direction. In some embodiments, the third and fourth straps 123 and 124 extend from respective third and fourth locations (see, e.g., locations 143 and 144 schematically illustrated in FIGS. 3-5) of the body portion spaced apart (by distance W0) along the width direction by greater than 0.3, 0.4, 0.5, 0.6, 0.65, 0.7, or 0.75 times a width W1 of the body portion along the width direction.

Similarly, in some embodiments of radiolucent mat 100, or 100', or 100" for the straps 123 and 124, each strap extends from a location on a side close to an edge of an adjacent side. In some embodiments, each of a largest separation s1 of the first location 141 from the third side 106 along the length direction and a largest separation s2 of the second location 142 from the fourth side 108 along the length direction is less than 0.3, 0.25, 0.2, 0.15, or 0.1 times the length L1 of the body portion 101. In some embodiments, each of a largest separation s3 of the third location 143 from the first side 102 along the width direction and a largest separation s4 of the fourth location 144 from the second side 104 along the width direction is less than 0.3, 0.25, 0.2, 0.15, or 0.1 times the width W1 of the body portion.

In some embodiments, the top major surface 151 includes one or more first visual indicia 110 delineating a region 171 of the top major surface 151 corresponding to an active region of the image receptor. The one or more first visual indicia 110 may be a rectangular box, for example, on the top major surface 151 outlining the region 171 or may be or include line segments delineating the sides of the rectangular region, for example. As described further elsewhere herein, the mat 100, 100', 100" can optionally further include indicia 112, 112' and/or 114. Any of the indicia 110, 112, 112' and/or 114 may be printed, for example, or otherwise applied to a major surface of the body portion 101. For example, the indica may be printed onto an outer cover of the body portion 101.

Figure 8:
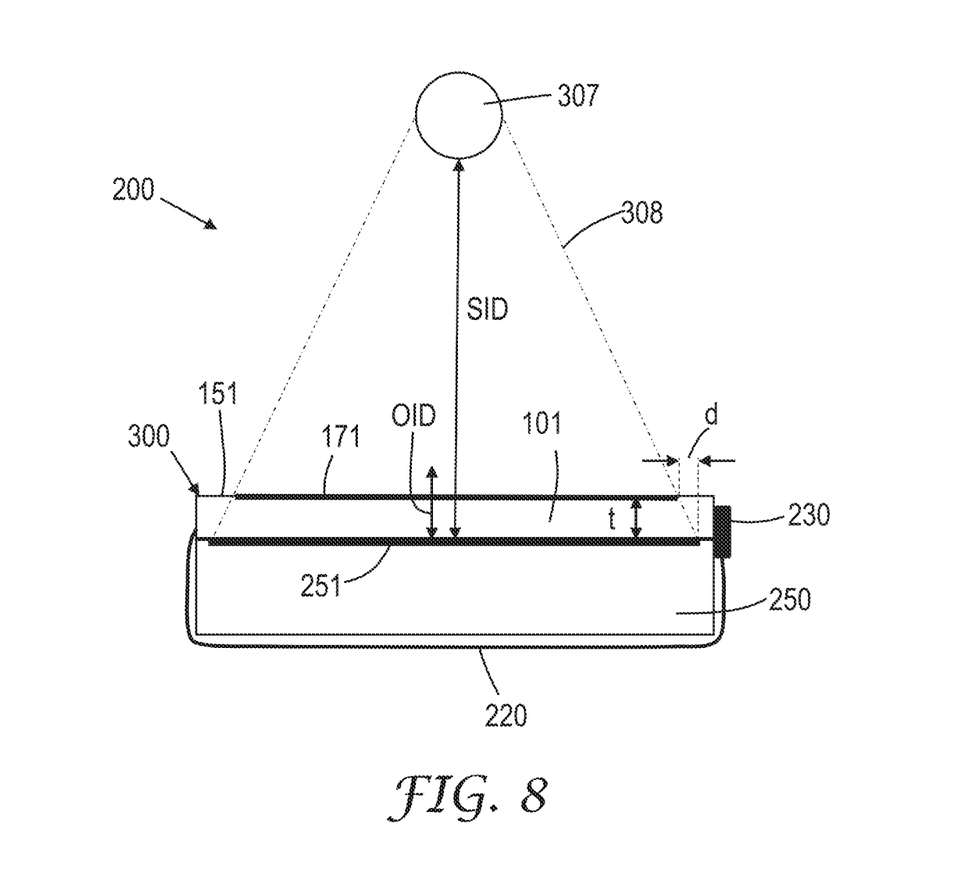
FIG. 8 is a schematic cross-sectional view of an image receptor assembly, according to some embodiments.
Figure 9:
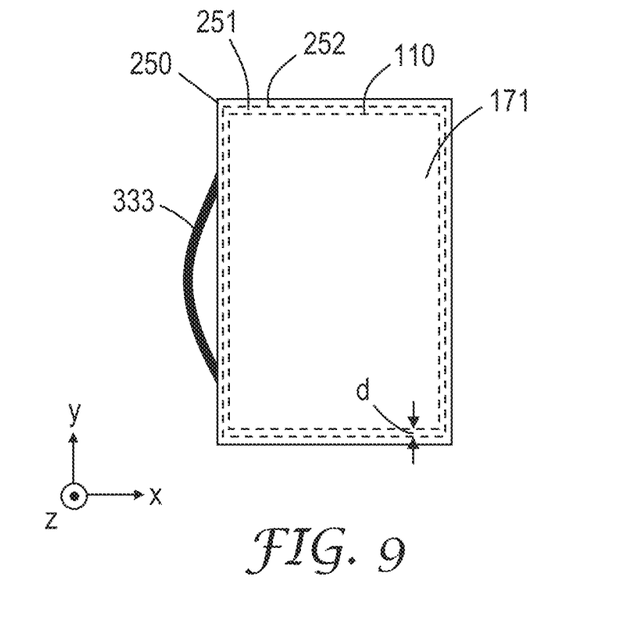
FIG. 9 is a schematic top plan view of a body portion of a radiolucent mat disposed on an image receptor, according to some embodiments.

A radiography image receptor 250 may have an active region 251 surrounded by a peripheral region that does not capture x-ray information (see, e.g., FIGS. 8-9). The active region 251 can have an orientation such that upper and lower regions of the active region 251 become respective upper and lower regions of the resulting image. In some embodiments, the radiolucent mat 100, 100', 100" includes one or more second visual indicia 112, 112' (see, e.g., FIGS. 2-4) disposed on the body portion 101 and including at least one indicum 112 disposed on the top major surface 151, where the one or more second visual indicia 112, 112' indicates an orientation of the active region 251. For example, the one or more second visual indicia 112, 112' can include one or more arrows to indicate the orientation. Each of the one or more second visual indicia 112, 112' is different than each of the one or more first visual indicia 110. In some embodiments, the one or more second visual indicia 112, 112' includes at least one indicum 112' disposed on a bottom major surface 152 of the body portion 101 opposite the top major surface 151. By using the one or more visual indicia 112, 112' the radiographer may align the upper region of the image receptor in relation to these symbols so that the resultant radiographs will show up on the imaging (e.g., computer) system anatomically correct from top to bottom without having to be flipped or vertically inverted on the imaging system.

In some embodiments, the mat 100, 100', 100" further includes one or more third visual indicia 114 disposed on the top major surface 151 (see, e.g., FIG. 2), where each third visual indicium 114 is different than each first and second visual indicium, and where at least the one or more third visual indicia distinguishes the top and bottom major surfaces 151 and 152.

Figure 6:
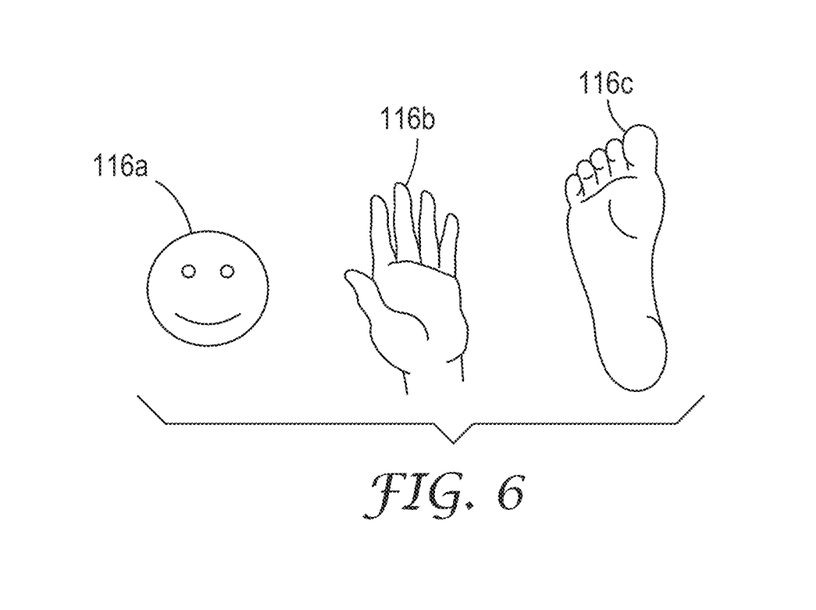
FIG. 6 is a schematic top view of visual indicia, according to some embodiments.

FIG. 6 is a schematic top view of visual indicia 116a, 116b, and 116c. The visual indicia 112 or 114, for example, may include any one, two, or all three of visual indicia 116a, 116b, and 116c (e.g., arranged in a row adjacent to the illustrated indicia 112 and 114 in FIG. 2). The visual indicia 116a, 116b, and 116c may indicate a proper orientation of an infant or body part(s) of an infant, for example, relative to an upper region of the image receptor. For example, the visual indicium 116a may indicate the (e.g., upper) region of the image receptor where the baby's head should face. The visual indicium 116b may indicate the (e.g., upper) region of the image receptor (e.g., the fingers of the illustrate hand can point generally in the direction of the upper region) where the baby's hand(s) should face. The visual indicium 116c may indicate the (e.g., upper) region of the image receptor (e.g., the toes of the illustrate foot can point generally in the direction of the upper region) where the baby's foot or feet should face. In some embodiments, the visual indica 112 and 114 of FIG. 2, for example, includes each of an up arrow (e.g., 112), a face (e.g., 114, 116a), a hand (e.g., 116b), and a foot (e.g., 116c).

Figure 7:
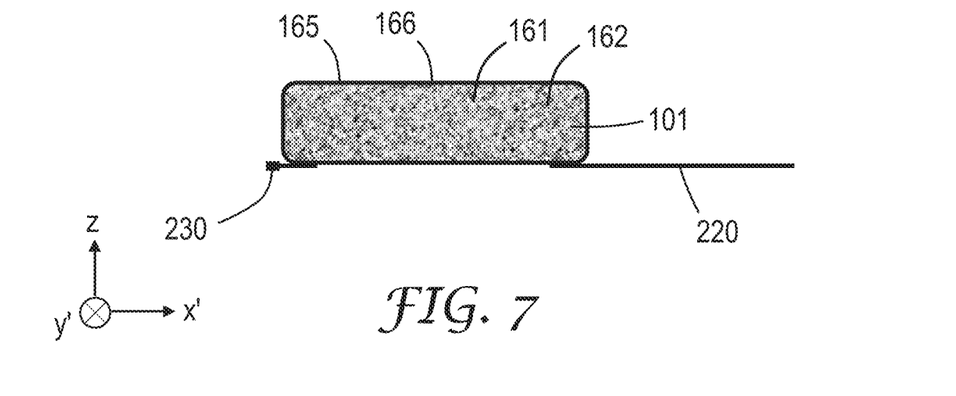
FIG. 7 is a schematic cross-sectional view a radiolucent mat, according to some embodiments.

FIG. 7 is a schematic cross-sectional view a radiolucent mat 100, 100', 100" according to some embodiments. The illustrated cross-section is in an x'-z plane which may correspond to the x-z or the y-z plane. A strap 220 and a connector 230 are schematically illustrated in FIG. 7. The strap 220 may correspond to any of straps 121-124 and the connector 230 may correspond to any corresponding connector 131-134. In some embodiments, the body portion 101 includes a cushioning material 161 disposed inside a cover 165. The first through fourth straps 121-124 and the first through fourth connectors 131-134 can be attached to the cover 165 via stitching (sewing) and/or bonding (e.g., via an adhesive). The cushioning material 161 may be or include a polymeric foam 162, for example. The cover 165 can be or include a polymeric fabric 166, for example.

The radiolucent mat 100, 100', 100" may be sufficiently radiolucent (transparent to x-rays, for example) so as to not significantly interfere with the imaging. The materials for the cushioning material 161 and the cover 165 can be selected from radiolucent materials known in the art. Certain types of plastics (e.g., unfilled polymers), for example, are generally radiolucent. In some embodiments, the cover 165 and/or the cushioning material 161 includes polyester, polypropylene, polyethylene, polyurethane, nylon, vinyl, polycarbonate, polyketone, or a combination thereof.

FIG. 8 is a schematic cross-sectional view of an image receptor assembly 200, according to some embodiments. The image receptor assembly 200 includes a radiolucent mat 300 which may correspond to any of radiolucent mats 100, 100', 100" and which includes a body portion 101 extending along orthogonal length (e.g., y'-direction) and width (e.g., x'-direction) directions of the body portion 101. The image receptor assembly 200 includes a radiography image receptor 250 having an active region 251. The body portion 101 can be disposed on the image receptor 250 such that the body portion 101 and the image receptor 250 are substantially coextensive with one another along the length and width directions (see, e.g., FIG. 9). The mat 300 includes a strap system (e.g., corresponding to any of 120, 120', 120") securing the mat to the image receptor 250 and preventing the mat from moving relative to the image receptor along each of the length and width directions. The body portion 101 includes a top major surface 151 facing away from the image receptor 250 where the top major surface 151 includes one or more visual indicia 110 (see, e.g., FIGS. 1-2) delineating a region 171 of the top major surface corresponding to the active region 251 of the image receptor 250. The image receptor 250 can be or include any image receptor known in the art. For example, the image receptor 250 can be or include a digital radiography digital image receptor, or a computed radiography photostimulable phosphor plate, or a film radiography image receptor. The strap 220 schematically illustrated in FIG. 8 may be tightened around the image receptor 250 and received in the connector 230 to secure the mat 300 in place.

FIG. 8 also schematically illustrates a radiation source 307, which may be or include an x-ray tube, a source to image distance SID (which is about 100 cm or 40 inches in many systems), and a typical object to image distance OID (e.g., distance between a bone being imaged and the active region 251). In some embodiments, the region 171 of the top major surface 151 is smaller than the active region 251 of the image receptor 250. The region 171 may be smaller than the active region 251 to account for the divergence of radiation 308 emitted from the radiation source 307.

The body portion 101 has an average thickness t. In some embodiments, in order to provide adequate cushioning to an infant, for example, the average thickness t may be at least 0.2, 0.25, or 0.3 inches. In some embodiments, in order to minimize the increase in the object to image distance OID due to the mat, for example, the average thickness t may be less than or equal to 0.8, 0.7, or 0.6 inches. For example. the average thickness t may be in a range of 0.2 inches to 0.8 inches, or 0.25 inches to 0.7 inches, or 0.3 inches to 0.6 inches.

FIG. 9 is a schematic top plan view of the body portion 101 of the radiolucent mat disposed on the image receptor 250, according to some embodiments. A boundary 252 of the active region 251 is indicated. The one or more indicia 110 delineates the region 171 of the top major surface 151. In some embodiments, the body portion 101 has an average thickness t in a thickness direction (z-direction) orthogonal to the length (y-direction) and width (x-direction) directions, and the region 171 of the top major surface 151 has at least one boundary offset from a corresponding boundary of the active region of the image receptor toward an interior of the region of the top major surface by a distance d in a range of 0.1 to 0.3 times the average thickness t. In some embodiments, the body portion 101 has an average thickness t in the thickness direction orthogonal to the length and width directions, where the active region 251 of the image receptor 250 and the region 171 of the of the top major surface 151 are respective first and second rectangular regions as schematically illustrated in FIG. 9. Each of the first and second rectangular regions has four sides, where each side of the second rectangular region (e.g., region 171) is offset from a corresponding side of the first rectangular region (e.g., region 251) toward an interior of the first rectangular region by a distance d in a range of 0.1 to 0.3 times the average thickness t.

In some embodiments, the image receptor 250 includes an optional handle 333. In some embodiments, the handle 333 obstructs the placement of straps along the length direction and a single strap is used along the length direction (see, e.g., FIG. 12). In other embodiments, two (or more) straps are used along the length direction even when the handle 333 is included (see, e.g., FIGS. 10-11).

Figure 10:
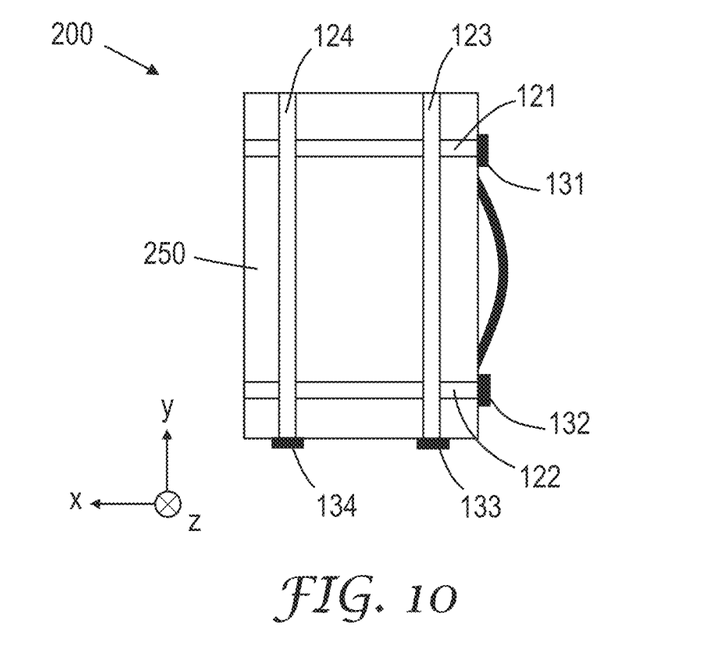
FIGS. 10-12 are schematic bottom views of image receptor assemblies, according to some embodiments.
Figure 11:
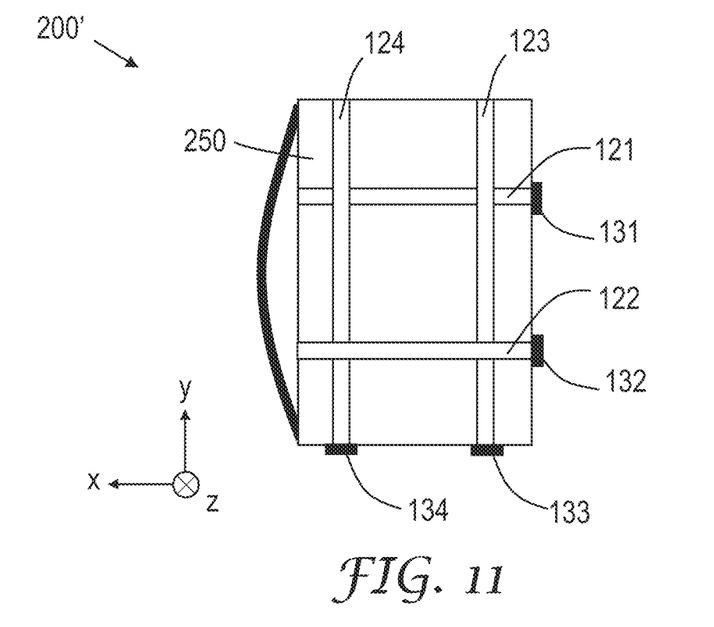
Figure 12:
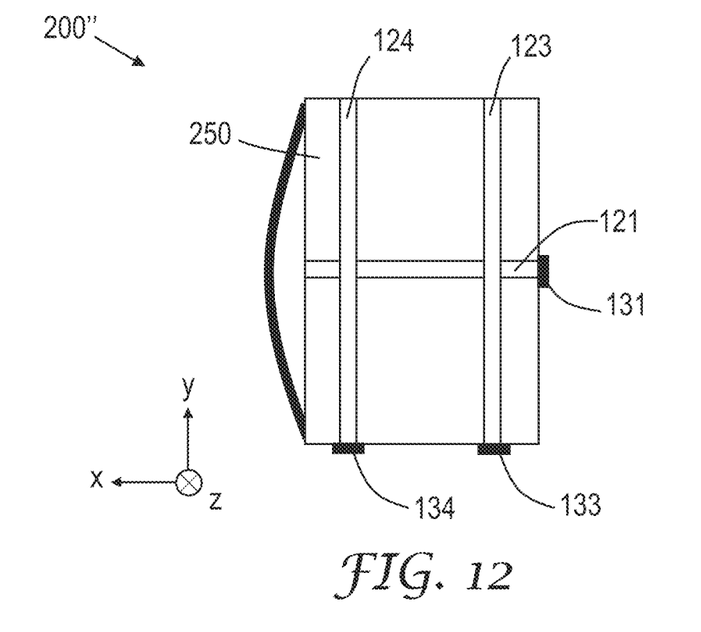

FIG. 10-12 are schematic bottom views of image receptor assembly 200, 200', and 200", according to some embodiments. In some embodiments, as described further elsewhere herein, the radiolucent mat 100, 100', 100" can include a strap system including a first strap 121 extending from a first side 102 of the body portion 101; a first connector 131 receiving the first strap 121 and disposed adjacent a second side 104 of the body portion opposite the first side 102, where the image receptor 250 is disposed between the body portion 101 and the first strap 121, and where the first and second sides extend along the length direction (y-direction) and are spaced apart along the width direction (x-direction); a second strap 122 extending from one of the first and second sides of the body portion; a second connector 132 receiving the second strap 122 and disposed adjacent the other of the first and second sides, where the image receptor 250 is disposed between the body portion 101 and the second strap 122, and where the first and second straps 121 and 122 extend from respective first and second locations of the body portion spaced apart along the length direction by greater than 0.3 times a length of the body portion of along the length direction; a third strap 123 extending from a third side 106 of the body portion 101; a third connector 133 receiving the third strap 123 and disposed adjacent a fourth side 108 of the body portion opposite the third side 106, where the image receptor 250 is disposed between the body portion 101 and the third strap 123, and where the third and fourth sides extend along the width direction and is spaced apart along the width direction; a fourth strap 124 extending from one of the third and fourth sides of the body portion; and a fourth connector 134 receiving the fourth strap 124 and disposed adjacent the other of the third and fourth sides, where the image receptor 250 is disposed between the body portion 101 and the fourth strap 124, and where the third and fourth straps 123 and 124 extend from respective third and fourth locations of the body portion spaced apart along the width direction by greater than 0.3 times a width of the body portion along the width direction.

In some embodiments, as described further elsewhere herein, the radiolucent mat 100" can include a strap system 120" including a first strap 121 extending from a first location 141 of a first side 102 of the body portion, where the first location 141 is substantially centered on the first side 102 along the length direction; a first connector 131 receiving the first strap 121 and disposed adjacent a second side 104 of the body portion 101 opposite the first side 102, where the first and second sides 102 and 104 extend along the length direction and are spaced apart along the width direction; a second strap 123 extending from a third side 106 of the body portion 101; a second connector 133 receiving the second strap 123 and disposed adjacent a fourth side 108 of the body portion 101 opposite the third side 106, where the third and fourth sides 106 and 108 extend along the width direction and are spaced apart along the length direction; a third strap 124 extending from one of the third and fourth sides of the body portion (e.g., from the third side 106 as schematically illustrated in FIG. 5 or from the fourth side 108 as schematically illustrated in FIG. 4); and a third connector 134 receiving the third strap 124 and disposed adjacent the other of the third and fourth sides, where the second and third straps extend from respective second and third locations 143 and 144 of the body portion spaced apart along the width direction by greater than 0.3 times a width of the body portion along the width direction.

Descriptions for elements in figures should be understood to apply equally to corresponding elements in other figures, unless indicated otherwise. Although specific embodiments have been illustrated and described herein, it will be appreciated by those of ordinary skill in the art that a variety of alternate and/or equivalent implementations can be substituted for the specific embodiments shown and described without departing from the scope of the present disclosure. This application is intended to cover any adaptations, or variations, or combinations of the specific embodiments discussed herein. Therefore, it is intended that this disclosure be limited only by the claims and the equivalents thereof.

What is claimed is:

1. A radiolucent mat comprising:
a strap system configured to secure the radiolucent mat to an image receptor; and
a body portion extending along orthogonal length and width directions of the body portion and wherein the body portion has a top major surface configured to face away from the image receptor, wherein the top major surface comprises one or more first visual indicia delineating a region of the top major surface corresponding to an active region of the image receptor, wherein the strap system comprises:
a first strap extending from a first side of the body portion;
a first connector for receiving the first strap disposed adjacent a second side of the body portion opposite the first side, the first and second sides extending along the length direction and spaced apart along the width direction;
a second strap extending from one of the first and second sides of the body portion;
a second connector for receiving the second strap disposed adjacent the other of the first and second sides, the first and second straps extending from respective first and second locations of the body portion spaced apart along the length direction by greater than 0.3 times a length of the body portion along the length direction;
a third strap extending from a third side of the body portion;
a third connector for receiving the third strap disposed adjacent a fourth side of the body portion opposite the third side, the third and fourth sides extending along the width direction and spaced apart along the length direction;

a fourth strap extending from one of the third and fourth sides of the body portion; and a fourth connector for receiving the fourth strap disposed adjacent the other of the third and fourth sides, the third and fourth straps extending from respective third and fourth locations of the body portion spaced apart along the width direction by greater than 0.3 times a width of the body portion along the width direction.

2. The radiolucent mat of claim 1, wherein the body portion has an average thickness in a range of 0.2 to 0.8 inches.

3. The radiolucent mat of claim 1, wherein each of a largest separation of the first location from the third side along the length direction and a largest separation of the second location from the fourth side along the length direction is less than 0.3 times the length of the body portion.

4. The radiolucent mat of claim 1, wherein each of a largest separation of the third location from the first side along the width direction and a largest separation of the fourth location from the second side along the width direction is less than 0.3 times the width of the body portion.

5. The radiolucent mat of claim 1, wherein the body portion comprises a cushioning material disposed inside a cover, wherein the first through fourth straps and the first through fourth connectors are attached to the cover.

6. The radiolucent mat of claim 1 further comprising one or more second visual indicia disposed on the body portion and comprising at least one indicum disposed on the top major surface, wherein the one or more second visual indicia indicate an orientation of the active region.

7. The radiolucent mat of claim 5, wherein the cushioning material comprises a polymeric foam.

8. The radiolucent mat of claim 5, wherein the cover comprises a polymeric fabric.

9. The radiolucent mat of claim 6, wherein the one or more second visual indicia comprises at least one indicum disposed on a bottom major surface of the body portion opposite the top major surface.

10. The radiolucent mat of claim 6 further comprising one or more third visual indicia disposed on the top major surface, wherein each third visual indicium are different than each first and second visual indicium, wherein at least the one or more third visual indicia distinguish the top and bottom major surfaces.

11. An image receptor assembly comprising:
a radiolucent mat comprising a body portion extending along orthogonal length and width directions of the body portion; and
a radiography image receptor having an active region, wherein the body portion is disposed on the image receptor such that the body portion and the image receptor are substantially coextensive with one another along the length and width directions, wherein the radiolucent mat comprises a strap system securing the radiolucent mat to the image receptor and preventing the radiolucent mat from moving relative to the image receptor along each of the length and width directions, wherein the body portion comprises a top major surface facing away from the image receptor, wherein the top major surface comprises one or more visual indicia delineating a region of the top major surface corresponding to the active region of the image receptor, and wherein the region of the top major surface is smaller than the active region of the image receptor.

12. The image receptor assembly of claim 11, wherein the body portion has an average thickness in a thickness direction orthogonal to the length and width directions, and wherein the region of the top major surface has at least one boundary offset from a corresponding boundary of the active region of the image receptor toward an interior of the region of the top major surface by a distance in a range of 0.1 to 0.3 times the average thickness.

13. The image receptor assembly of claim 11, wherein the body portion has an average thickness in a thickness direction orthogonal to the length and width directions, wherein the active region of the image receptor and the region of the of the top major surface are respective first and second rectangular regions, wherein each of the first and second rectangular regions have four sides, and wherein each side of the second rectangular region is offset from a corresponding side of the first rectangular region toward an interior of the first rectangular region by a distance in a range of 0.1 to 0.3 times the average thickness.

14. The image receptor assembly of claim 11, wherein the strap system comprises:
a first strap extending from a first location of a first side of the body portion, the first location substantially centered on the first side along the length direction;
a first connector receiving the first strap and disposed adjacent a second side of the body portion opposite the first side, the first and second sides extending along the length direction and spaced apart along the width direction;
a second strap extending from a third side of the body portion;
a second connector receiving the second strap and disposed adjacent a fourth side of the body portion opposite the third side, the image receptor disposed between the body portion and the second strap, the third and fourth sides extending along the width direction and spaced apart along the width direction;
a third strap extending from one of the third and fourth sides of the body portion; and
a third connector receiving the third strap and disposed adjacent the other of the third and fourth sides, the image receptor disposed between the body portion and the third strap, the second and third straps extending from respective third and fourth locations of the body portion spaced apart along the width direction by greater than 0.3 times a width of the body portion along the width direction.

15. The image receptor assembly of claim 11, wherein the strap system comprises:
a first strap extending from a first side of the body portion;
a first connector receiving the first strap and disposed adjacent a second side of the body portion opposite the first side, wherein the radiography image receptor is disposed between the body portion and the first strap, and wherein the first and second sides extend along the length direction and are spaced apart along the width direction;
a second strap extending from one of the first and second sides of the body portion;
a second connector receiving the second strap and disposed adjacent the other of the first and second sides, wherein the radiography image receptor is disposed between the body portion and the second strap, and wherein the first and second straps extend from respective first and second locations of the body portion spaced apart along the length direction by greater than 0.3 times a length of the body portion of along the length direction;
a third strap extending from a third side of the body portion;
a third connector receiving the third strap and disposed adjacent a fourth side of the body portion opposite the third side, wherein the radiography image receptor is disposed between the body portion and the third strap, and wherein the third and fourth sides extend along the width direction and are spaced apart along the width direction;
a fourth strap extending from one of the third and fourth sides of the body portion; and
a fourth connector receiving the fourth strap and disposed adjacent the other of the third and fourth sides, wherein the radiography image receptor is disposed between the body portion and the fourth strap, and wherein the third and fourth straps extend from respective third and fourth locations of the body portion spaced apart along the width direction by greater than 0.3 times a width of the body portion along the width direction.

16. The image receptor assembly of claim 11, wherein the image receptor comprises a digital radiography digital image receptor.

17. The image receptor assembly of claim 11, wherein the image receptor comprises a computed radiography photostimulable phosphor plate.

18. The image receptor assembly of claim 11, wherein the image receptor comprises a film radiography image receptor.

19. The image receptor assembly of claim 13, wherein the average thickness of the body portion is in a range of 0.2 to 0.8 inches.

* * * * *